(12) United States Patent
Baturin et al.

(10) Patent No.: US 9,907,524 B2
(45) Date of Patent: Mar. 6, 2018

(54) MATERIAL DECOMPOSITION TECHNIQUE USING X-RAY PHASE CONTRAST IMAGING SYSTEM

(71) Applicant: Carestream Health, Inc., Rochester, NY (US)

(72) Inventors: Pavlo Baturin, Rochester, NY (US); Mark E. Shafer, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 51 days.

(21) Appl. No.: 14/874,748

(22) Filed: Oct. 5, 2015

(65) Prior Publication Data

US 2016/0095562 A1 Apr. 7, 2016

Related U.S. Application Data

(60) Provisional application No. 62/060,045, filed on Oct. 6, 2014.

(51) Int. Cl.
*A61B 6/00* (2006.01)

(52) U.S. Cl.
CPC ............ *A61B 6/484* (2013.01); *A61B 6/4291* (2013.01); *A61B 6/481* (2013.01)

(58) Field of Classification Search
CPC .................................................... A61B 6/484
See application file for complete search history.

(56) References Cited

U.S. PATENT DOCUMENTS

| 5,812,629 | A | 9/1998 | Clauser |
| 6,560,309 | B1 | 5/2003 | Becker et al. |
| 7,346,204 | B2 | 3/2008 | Ito |
| 7,453,981 | B2 | 11/2008 | Baumann et al. |
| 7,639,786 | B2 | 12/2009 | Baumann et al. |
| 7,646,843 | B2 | 1/2010 | Popescu et al. |
| 7,693,256 | B2 | 4/2010 | Brahme et al. |
| 7,817,777 | B2 | 10/2010 | Baumann et al. |
| 8,515,002 | B2 | 8/2013 | Huang et al. |
| 8,855,395 | B2 | 10/2014 | Baturin et al. |
| 9,001,967 | B2 | 4/2015 | Baturin et al. |
| 9,357,975 | B2 | 6/2016 | Baturin et al. |

(Continued)

FOREIGN PATENT DOCUMENTS

| DE | 102006015356 | 8/2007 |
| EP | 1731099 | 12/2006 |

(Continued)

OTHER PUBLICATIONS

H.N. Cardinal and A. Fenster "An accurate method for direct dual-energy calibration and decomposition" Medical Physics, May-Jun. 1990; vol. 17, No. 3, pp. 327-341.

(Continued)

*Primary Examiner* — Dani Fox

(57) ABSTRACT

A phase contrast x-ray imaging system generates an absorption image and a phase shift image of an object under study. The absorption image represents a measurement of the imaged object's attenuation of radiographic energy, and the phase shift image represents a measurement of the imaged object's phase shifting of the radiographic waves passing through the object. The two images may be used to improve soft tissue discrimination in radiographic imaging.

15 Claims, 10 Drawing Sheets

(56) References Cited

U.S. PATENT DOCUMENTS

| | | |
|---|---|---|
| 9,494,534 B2 | 11/2016 | Baturin et al. |
| 2005/0249328 A1 | 11/2005 | Bruder et al. |
| 2007/0183560 A1 | 8/2007 | Popescu et al. |
| 2007/0183582 A1 | 8/2007 | Baumann et al. |
| 2007/0183583 A1 | 8/2007 | Baumann et al. |
| 2008/0009717 A1 | 1/2008 | Herrmann et al. |
| 2008/0014643 A1 | 1/2008 | Bjorkholm |
| 2008/0075228 A1* | 3/2008 | Tasaki .................. A61B 6/4494 378/37 |
| 2008/0123805 A1 | 5/2008 | Zellerhoff |
| 2008/0273653 A1 | 11/2008 | Niwa et al. |
| 2009/0092227 A1 | 4/2009 | David et al. |
| 2009/0097730 A1* | 4/2009 | Kasai .................. A61B 6/00 382/132 |
| 2009/0116720 A1 | 5/2009 | Ritman |
| 2010/0220832 A1 | 9/2010 | Ning et al. |
| 2010/0220834 A1 | 9/2010 | Heismann et al. |
| 2010/0246764 A1 | 9/2010 | Itoh et al. |
| 2010/0246765 A1 | 9/2010 | Murakoshi et al. |
| 2010/0272235 A1 | 10/2010 | Takahashi |
| 2011/0085639 A1 | 4/2011 | Nakamura et al. |
| 2011/0135057 A1 | 6/2011 | Mori et al. |
| 2011/0206181 A1 | 8/2011 | Linev |
| 2011/0243305 A1 | 10/2011 | Tada |
| 2012/0020461 A1 | 1/2012 | Roessl et al. |
| 2012/0045108 A1 | 2/2012 | Shechter |
| 2012/0057677 A1 | 3/2012 | Vogtmeier et al. |
| 2012/0093284 A1 | 4/2012 | Takemoto et al. |
| 2012/0114098 A1 | 5/2012 | Mikami et al. |
| 2012/0163554 A1 | 6/2012 | Tada |
| 2012/0250972 A1 | 10/2012 | Tada et al. |
| 2013/0010926 A1 | 1/2013 | Tada |
| 2013/0028378 A1 | 1/2013 | Stutman et al. |
| 2013/0156284 A1 | 6/2013 | Koehler et al. |
| 2013/0259194 A1* | 10/2013 | Yip .................. A61B 6/502 378/37 |
| 2013/0308750 A1 | 11/2013 | Ishii |
| 2014/0044234 A1 | 2/2014 | Hashimoto et al. |
| 2014/0177789 A1 | 6/2014 | Baturin et al. |
| 2014/0185746 A1 | 7/2014 | Baturin et al. |
| 2014/0185896 A1 | 7/2014 | Baturin et al. |
| 2014/0226782 A1 | 8/2014 | Stutman et al. |
| 2014/0226783 A1 | 8/2014 | Ning et al. |
| 2014/0226785 A1 | 8/2014 | Stutman et al. |
| 2014/0270060 A1 | 9/2014 | Date et al. |
| 2014/0270061 A1 | 9/2014 | Yamaguchi |
| 2014/0341347 A1 | 11/2014 | Radicke |
| 2014/0355740 A1 | 12/2014 | Koehiler et al. |
| 2015/0092916 A1 | 4/2015 | Baturin et al. |
| 2015/0110247 A1 | 4/2015 | Baturin et al. |
| 2015/0117599 A1 | 4/2015 | Yun et al. |
| 2015/0131777 A1 | 5/2015 | Makifuchi et al. |
| 2015/0187096 A1 | 7/2015 | Baturin et al. |
| 2015/0216499 A1 | 8/2015 | Martens et al. |
| 2016/0038107 A1 | 2/2016 | Baturin et al. |
| 2016/0095562 A1 | 4/2016 | Baturin et al. |
| 2016/0125599 A1 | 5/2016 | Stampanoni et al. |

FOREIGN PATENT DOCUMENTS

| | | |
|---|---|---|
| WO | 2011/122715 | 10/2011 |
| WO | 2012/029048 | 3/2012 |
| WO | 2012/080125 | 6/2012 |
| WO | 2013/126296 | 8/2013 |
| WO | 2014/137318 | 9/2014 |

OTHER PUBLICATIONS

International Search Report, International application No. PCT/US2014/066027, dated May 2, 2015, 2 pages.
International Search Report, International application No. PCT/US2014/066033, dated Apr. 28, 2015, 2 pages.
International Search Report, International application No. PCT/US2013/026301, dated Jun. 3, 2013, 3 pages.
International Search Report, International application No. PCT/US2013/075898, dated Apr. 22, 2014, 2 pages.
Supplementary European Search Report, dated Nov. 27, 2015, European Application No. 13769560.7, 2 pages.
Thomas Thuring, Compact X-ray grating interferometry for phase and dark-field computed tomography in the diagnostic energy range, Swiss Federal Institute of Technology Zurich, 2013, pp. 1-180.
Thomas Thuring, et al., Non-linear regularized phase retrieval for unidirectional X-ray differential phase contrast radiography, Optics Express, vol. 19, Issue 25, pp. 25545-25558, Optical Society of America 2011, issn: 10944087.
C. Kottler et al., Grating interferometer based scanning setup for hard x-ray phase contrast imaging, Review of Scientific Instruments, vol. 78, 034710, 2007, pp. 1-4.
Chapman, D., Thomlinson, et al., "Diffraction enhanced x-ray imaging," Phys. Med. Biol., 42, 2015, (1997).
Bonse, et al., "An x-ray interferometer," Appl. Phys. Lett. 6(8), 155-156, (1965).
Ingal. V. N., et al., "X-ray plane-wave topography observation of the phase contrast from non-crystalline object," J. Phys. D 28(11), 2314-2317, (1995).
Wilkins, S. W., et al., "Phase-contrast imaging using polychromatic hard X-rays," Nature (London) 384(6607) 335-338, (1996).
Momose, A., et al., "Demonstration of X-ray Talbot interferometry," Jpn. J. Appl. Phys. 42, L866-L868, (2003).
Wietkamp, T., et al., "X-ray phase imaging with a grating interferometer," Opt. Exp. 13(16), 6296-6304, (2006).
Pfeiffer, F., "Phase retrieval and differential phase-contrast imaging with low-brilliance X-ray sources", Nature Phys. 2, 258-261, (2006).
International Search Report, International application No. PCT/US2016/062389, dated Feb. 2, 2017, 2 pages.
Jian Fu, et al., Helical differential X-ray phase-contrast computed tomography, Physica Medica, vol. 30, pp. 374-379, 2014.

\* cited by examiner

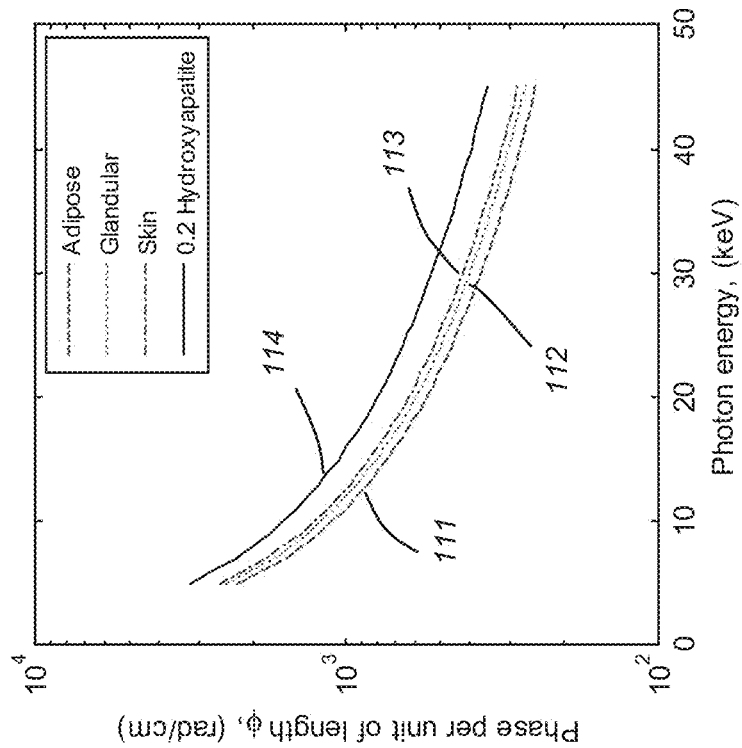
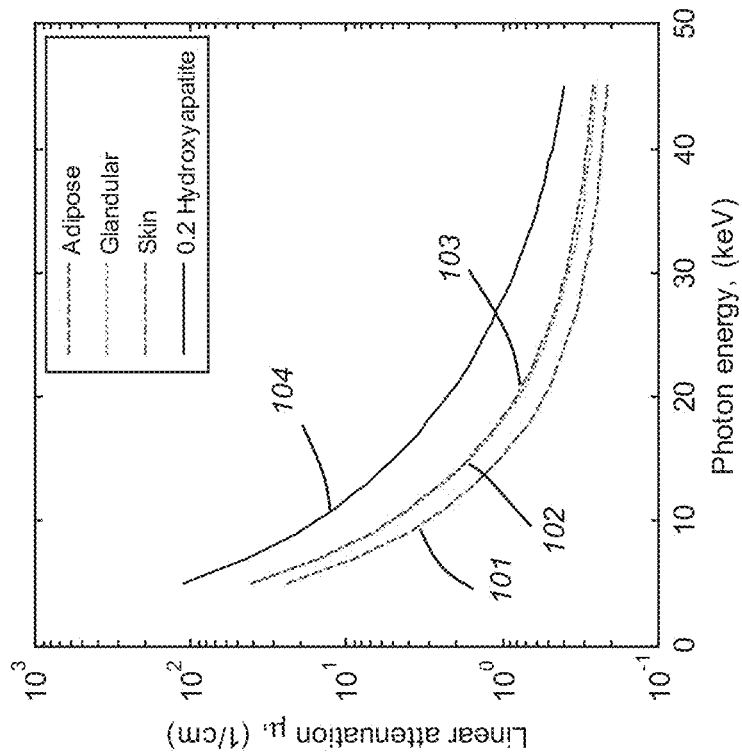
FIG. 1B
FIG. 1A

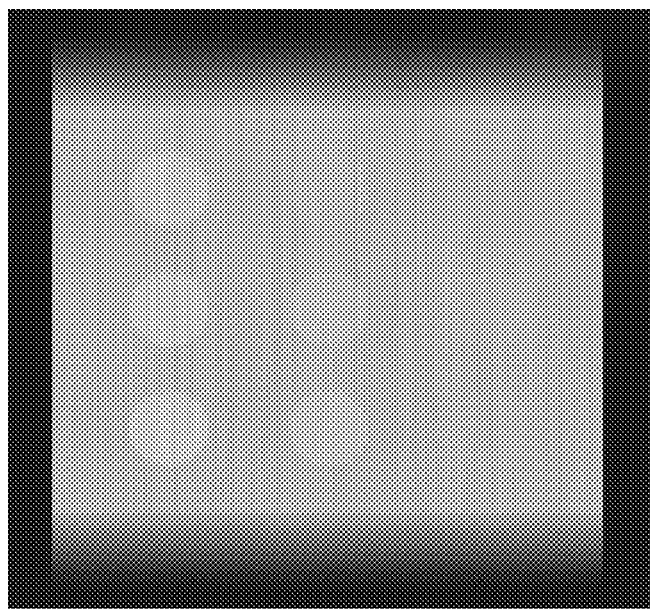
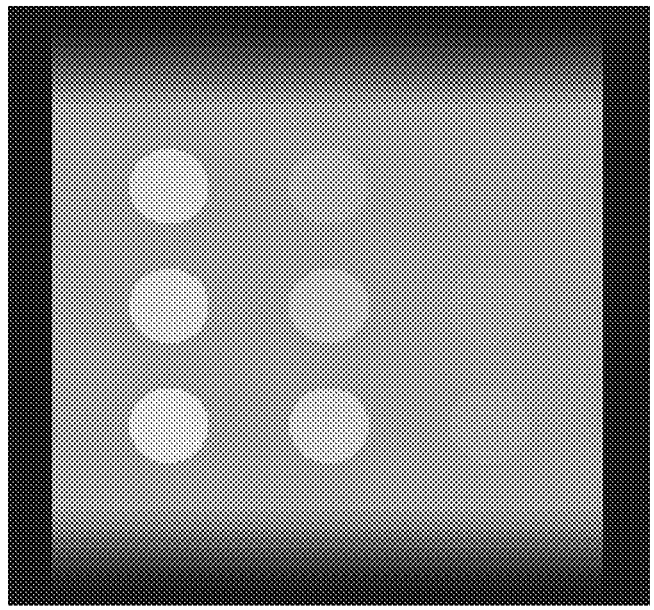
*FIG. 7A*
*FIG. 7B*

MATERIAL DECOMPOSITION TECHNIQUE USING X-RAY PHASE CONTRAST IMAGING SYSTEM

CROSS REFERENCE TO RELATED APPLICATIONS

This application claims priority to U.S. Patent Application Ser. No. 62/060,045, filed Oct. 6, 2014, in the name of Baturin et al., and entitled MATERIAL DECOMPOSITION TECHNIQUE USING X-RAY PHASE CONTRAST IMAGING SYSTEM.

This application is related in certain respects to U.S. patent application Ser. No. 14/499,762, filed Sep. 29, 2014, in the name of Baturin et al., and entitled MATERIAL DIFFERENTIATION WITH PHASE CONTRAST IMAGING; U.S. patent application Ser. No. 13/732,767, filed Jan. 2, 2013, in the name of Baturin et al., and entitled CONDITIONAL LIKELIHOOD MATERIAL DECOMPOSITION AND METHODS OF USING THE SAME; U.S. patent application Ser. No. 13/729,443, filed Dec. 28, 2012, in the name of Baturin et al., and entitled SPECTRAL GRATING-BASED DIFFERENTIAL PHASE CONTRAST SYSTEM FOR MEDICAL RADIOGRAPHIC IMAGING; U.S. patent application Ser. No. 13/724,096, filed Dec. 21, 2012, in the name of Baturin et al., and entitled GRATING-BASED DIFFERENTIAL PHASE CONTRAST IMAGING SYSTEM WITH ADJUSTABLE CAPTURE TECHNIQUE FOR MEDICAL RADIOGRAPHIC IMAGING; all four of which are incorporated herein by reference in their entirety.

BACKGROUND OF THE INVENTION

The subject matter disclosed herein relates to phase contrast imaging (PCI), in particular, to PCI imaging techniques to improve soft tissue discrimination using x-rays.

Material differentiation is an important task in the field of diagnostic medical imaging. Discriminating between two or three materials, sometimes more, may be required to reconstruct a 3D material morphology of a scanned object. There are numerous biomedical applications where material differentiation is necessary. For example, material identification may be necessary for: identification of contrast materials in cardiovascular imaging, such as iodine or other contrast agents, e.g., gold nanoparticles; identification of cancerous tumors or assessment of breast density in digital mammography; and identification of kidney stones in renal imaging, among others.

A dual energy x-ray technique is one known method that is used to provide such material differentiation. Such a method requires a plurality of x-ray exposures for the object being imaged. At least one of the exposures is taken at a lower energy of the x-ray beam and another identical exposure is taken at a relatively higher energy setting. In another method, a single x-ray scan uses a photon-counting energy-resolving detector, where the measurement of the emitted x-ray energy spectrum is logically separated by the detector's electronic comparator circuits into energy bins, which is often referred to as spectral measurement. Since it is desirable to minimize the number of x-ray exposures experienced by patients and because photon-counting energy-resolving detectors are not yet readily clinically accessible, there remains a need for the development of a single PCI exposure method, technique and/or apparatus capable of reliably differentiating between two, three, or more, scanned materials using charge integrating flat panel detectors.

The discussion above is merely provided for general background information and is not intended to be used as an aid in determining the scope of the presently claimed subject matter.

BRIEF DESCRIPTION OF THE INVENTION

A phase contrast x-ray imaging system generates an absorption image and a phase shift image of an object under study. The absorption image represents a measurement of the imaged object's attenuation of radiographic energy, and the phase shift image represents a measurement of the imaged object's phase shifting of the radiographic waves passing through the object. The two images may be used to improve soft tissue discrimination in radiographic imaging. In one aspect, embodiments disclosed herein advance the art of medical radiographic imaging, address in whole or in part at least the foregoing and other deficiencies in the related art, and address in whole or in part at least the advantages described herein. An advantage that may be realized in the practice of one or more disclosed embodiments of the invention is improved imaging contrast of soft tissues in radiographic images.

In one embodiment, a method comprises radiographically scanning an object using a PCI imaging system. A plurality of radiographic images are generated by the scanning, including a first image of the object that represents levels of absorption of the radiographic radiation by the object, and a second image that represents phase shifting of the radiographic radiation by the object.

In another embodiment, a phase contrast imaging system comprises a radiographic energy source and a flat panel digital detector configured to radiographically expose an object to produce a plurality of radiographic images of the object. A first one of the produced images is generated by a measurement of the object's attenuation of the radiographic energy, while a second one of the produced images is generated by a measurement of a phase shift of the radiographic energy passing through the object.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIGS. 1A-1B are graphs plotting the linear attenuation and phase shift per unit of length (1/cm) for adipose, glandular, skin, and 20% mixture of hydroxyapatite;

FIGS. 7A-7B are diagrams of exemplary reconstructed attenuation and phase images, respectively;

DETAILED DESCRIPTION OF THE INVENTION

Conventional medical x-ray imaging devices rely on x-ray absorption properties of the scanned object to provide the information about the interior structure of the object. Such absorption type of imaging assumes that non-refractive x-rays pass through the object under study and their energy level is measured at a digital electronic detector. The contrast in the images thus obtained by the detector is produced due to the differences in the material absorption cross section. While generally good contrast between highly attenuating (hard) and weakly attenuating (soft) materials is observed, the imaging differentiation (contrast) between soft-tissue materials can be difficult to produce due to their lower relative absorption. For example, the low-contrast soft tissue materials including, but not limited to, vessels, cartilages, lungs, and breast tissues provide poor contrast in comparison to highly attenuating bone structures. The problem of low soft-tissue imaging contrast may be addressed by using interferometric x-ray imaging devices, which utilize, or manipulate, the electromagnetic wave nature of x-ray radiation. Such imaging interferometers focus on measuring the refraction characteristics manifested by x-rays passing through the object of study. In addition to conventional absorption images, these devices can provide differential phase contrast imaging (DPCI) and dark-field imaging. A DPCI image contains information about the x-ray phase shifting properties of the object of study, while an absorption image contains complementary attenuation information about the object's material properties. A dark-field image contains information about the local scattering or diffraction of x-rays within the object.

Turning to methods of processing and/or calculating the attenuation and phase shift information captured by the radiographic imaging systems described herein, the refraction properties of x-rays penetrating a material object can be described by an index of refraction n, represented by the complex number $$n = 1 - \delta + i\beta \tag{1}$$

where the imaginary part $\beta$ contributes to the attenuation of the amplitude (absorption) and the real part $\delta$ (refraction index decrement) contributes to the phase shift. While the interferometer type of imaging devices, such as PCI, can measure both $\beta$ and $\delta$ terms, conventional imaging devices can detect only $\beta$, measured in 1/cm units. It can be shown that $\delta$, measured in rad/cm units, is about $10^3$ to $10^4$ times larger than $\beta$. This fact provides the potential for generating images of soft-tissue materials with higher contrast.

Figure 3:
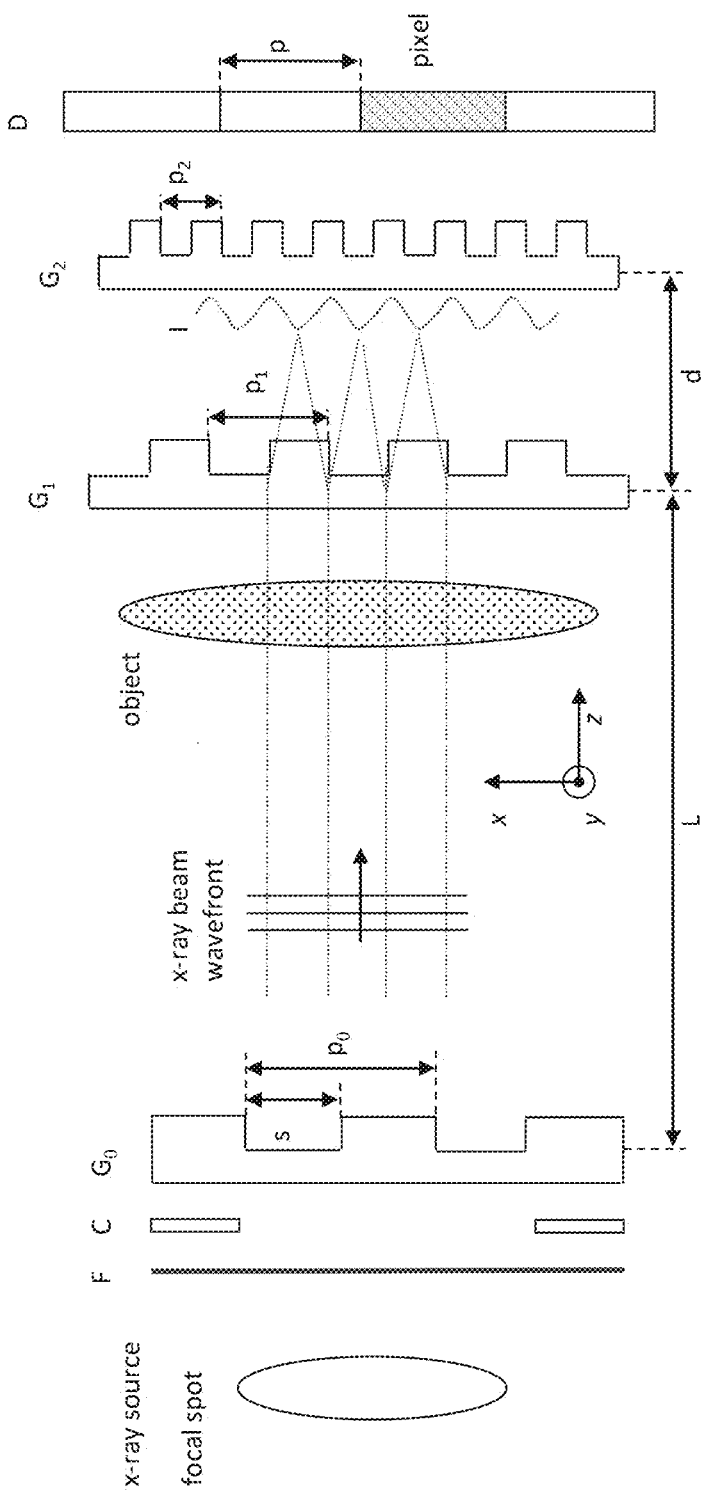
FIG. 3 is a schematic diagram of a three-grating PCI system with gratings G0, G1, and G2, an x-ray detector D, additional filtration F, and collimator C.

When the x-ray is passing through the material of the imaged object, its captured attenuation and phase shift information can be represented, or calculated, as:

$$\begin{cases} \mu(x,y) = \frac{4\pi}{\lambda} \int \beta(x,y,z) dz \\ \varphi(x,y) = \frac{2\pi}{\lambda} \int \delta(x,y,z) dz \end{cases} \tag{2}$$

respectively, using as reference the x, y, z axes shown in FIG. 3. For a material of density $\rho$ the refractive index can be expressed in terms of the tabulated atomic scattering factors $f_1$ and $f_2$:

$$n \cong 1 - \frac{r_e N_a \lambda^2 \rho}{2\pi} \left( \sum_k x_k (f_{1,k} + i f_{2,k}) \right) / \left( \sum_k x_k A_k \right) \tag{3}$$

where $r_e$, $N_a$, $\lambda$, and $\rho$ are the electron radius, Avogadro number, photon wavelength, and effective density of the material, respectively. The summation may be taken over the relative concentrations $x_k$ of each of the chemical elements of atomic mass $A_k$ comprising the material. While scattering may disrupt coherence of the x-rays, it is not predominant.

To date, several PCI techniques have been explored, including: the interferometer technique, the diffraction-enhanced imaging (DEI) technique, and the free-space propagation technique. However, there are various practical problems associated with these three techniques. In the case of crystal interferometers and diffractometers, high temporal coherence of the x-ray source (i.e., a high degree of monochromaticity) is required which limits such applications to a synchrotron radiation or a well defined monochromatic radiation source. In addition to the requirement of a synchrotron source, the use of a multi-hole collimator in DEI limits the achievable spatial resolution and increases the image acquisition time. Finally, the free-space propagation technique is limited in efficiency due to a requirement for high spatial coherence of the x-ray source, which may only be obtained by using an x-ray source with a very small focal spot size or using a large propagation distance. In addition to the techniques mentioned herein, a grating based differential phase contrast interferometry based on Talbot-Lau principles has been actively explored. Such an imaging device may utilize a standard broadband x-ray tube when used together with a partially absorbing grating G0 (source grating), which can generate partially coherent x-ray radiation. The refraction characteristics of a scanned object in such a system are detected via interference patterns, generated by a phase grating G1 and modulated onto a digital imaging detector by partially absorbing grating G2, as shown in FIG. 3.

The image acquisition procedures in the techniques described above typically require a plurality of x-ray exposures. These methods may also require at least some of the geometrical parameters to be altered with each x-ray exposure when conducting a scan, for example. In another example, grating based inteferometry may require at least one of the three gratings to be translated (or stepped) with respect to the rest of the system. Such an acquisition technique may be referred to herein as phase stepping. The direction of the stepping may be perpendicular to a lengthwise direction of the trenches, or slots, in the grating. Using phase stepping, the acquisition process may result in three images: a transmittance image (absorption image); a differential phase image ($\phi$); and a dark-field image. The transmittance image represents a mean intensity of the x-ray energy measured by the detector over a phase-stepping cycle. For example, if six images are captured over a phase-stepping cycle (FIG. 4), the average intensity of the six images may be calculated to generate the transmittance (absorption) image. The differential phase image represents a gradient of x-ray phase shift occurring in the object in the direction of phase stepping (i.e., the direction of the grating's translation). The dark-field image reproduces the intensity modulation observed during the phase stepping relative to the mean intensity (or contribution of the scattering effects).

The information carried by each of the images may be significantly different from each other. As disclosed herein, the phase shift of the x-rays passing through the object, which is proportional to a refraction index decrement $\delta$ of the object material, is of a particular interest since it can provide better soft-tissue image contrast. To obtain such phase shift information, the differential phase image may be integrated along the differential direction, e.g. perpendicular to a lengthwise direction of the grating slots and along the direction of phase stepping movement.

Attenuation (or absorption) and phase shift information represent two independent properties of the object of study which are exhibited by x-rays passing through the object. When properly combined, these properties assist in the task of material differentiation. Current material differentiation techniques primarily use attenuation properties of the object with respect to x-rays passing therethrough and rely on two facts: 1) the absorption of the material of the object is a function of the x-ray energy and 2) the energy dependence of absorption varies among different materials. Some techniques, for example, the dual energy technique described herein, exploit these properties by using at least two x-ray exposures taken at different x-ray beam energies, e.g., relatively low and high energies, to predict a distribution of different materials in the scanned object. The plurality of x-ray exposures may be avoided if an energy resolving detector is used, for example, a Cd—Te or Cd—Zn—Te photon-counting detector. In such energy-resolving detectors the plurality of energy dependent information is captured and separated into so-called energy bins, where a detected x-ray beam is logically divided into individual energy ranges (bins) defined by the detector's electronic comparator circuits. If a charge-integrating detector is used, the plurality of x-ray exposures is necessary to obtain absorption measurement at different energies, e.g., low and high. The structure of such digital flat panel detectors, including their two dimensional array of photosensitive pixels for capturing radiographic energy is well known and not described further.

Similar to the absorption technique described herein, the x-ray beam phase shift through the object under study is energy dependent. The energy dependence varies from one material to another. These properties allow use of the phase shift information, in addition to absorption information, to generate multiple images of the object under study and may eliminate the necessity of plural x-ray exposures at each imaging position, i.e., low and high energy exposures. Thus, a single PCI exposure as described herein may be substituted for the plurality of x-ray exposures.

In the case of the absorption based dual energy technique requiring low and high energy exposures, the at least two x-ray measurements should have sufficient difference (separation) between their mean energies, i.e., the separation between low and high energies. The separation is a key factor that affects the quality of the obtained material decomposition. Another factor affecting the material differentiation is the material's energy dependence. For example, it may be difficult to differentiate between two materials which exhibit very similar energy dependencies, i.e., their energy dependence curves are very close to each other. In contrast to an absorption based system, a phase shift system may provide a larger gap between such energy dependence curves and so a better material differentiation can be achieved when processing the captured image information. Again, the PCI would not require a plurality of x-ray exposures at different energies and one PCI scan at a single energy would be sufficient.

Figure 2:
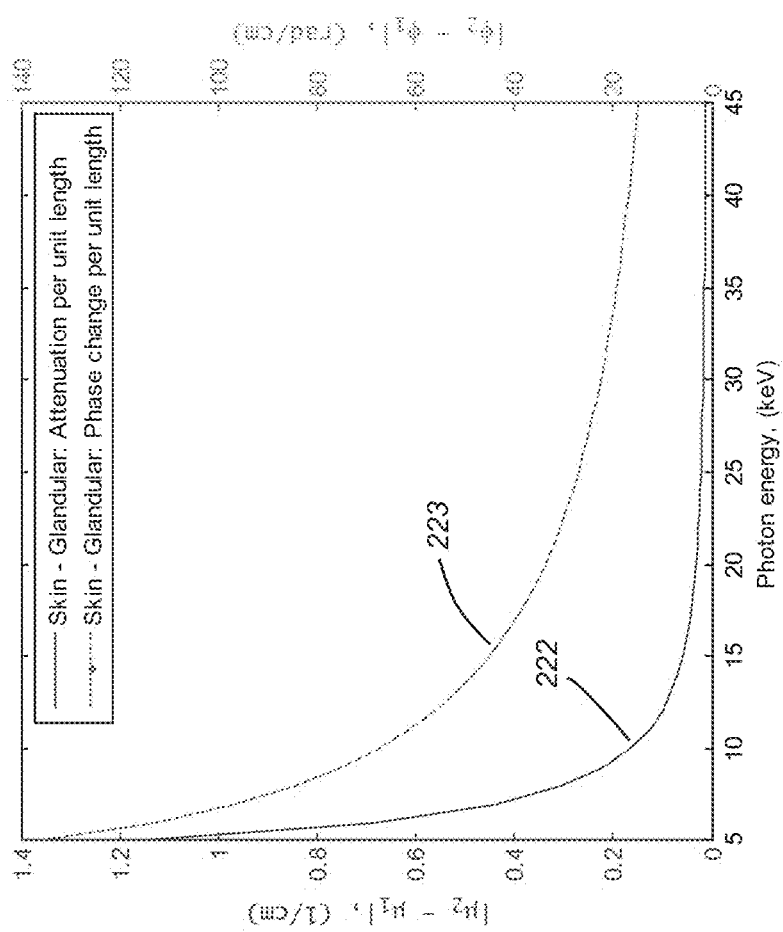
FIG. 2 is a graph plotting absorption (left vertical axis) and phase contrast (right vertical axis) between two exemplary materials: skin and glandular tissue.

FIGS. 1A and 1B show the linear attenuation and the phase shift, respectively, per unit of length over a range of x-ray energies for materials that are known and may be common for a human breast: adipose tissue 101, 111, glandular tissue 102, 112; skin 103, 113; and 20% hydroxyapatite water-based mixture 104, 114, which may represent, e.g., a calcification. Although, the breast is chosen as an example, any other materials may be used without loss of generality. As shown in FIGS. 1A-1B, the phase shift data is significantly higher than the absorption data by a few orders. FIG. 2 shows an example of the contrast between two materials, glandular tissue and skin, which have very similar attenuation curves and may be inseparable, or indistinguishable, in standard absorption images. The difference between material linear attenuations, glandular tissue and skin, is plotted on the left, 222, while the difference in their phase is plotted on the right, 223. The curve for difference in phase shift, 223, is significantly higher than the one for difference in absorption, 222. Therefore, the image of the material's phase shift may provide a better material differentiation after being processed using the representative formulas and equations disclosed herein.

The absorption and phase shift data of FIGS. 1A-1B are tabulated in Table 1, below, for photon energies 20, 30, and 40 keV. Additionally, the two-material absorption and phase shift difference data of FIG. 2 are shown below in Table 2.

TABLE 1

Material attenuation and phase change per unit of length

| Energy, (keV) | Adipose | | Glandular | | Skin | | 0.2 Hydroxyapatite | |
|---|---|---|---|---|---|---|---|---|
| | μ, (1/cm) | φ, (rad/cm) | μ, (1/cm) | φ, (rad/cm) | μ, (1/cm) | φ, (rad/cm) | μ, (1/cm) | φ, (rad/cm) |
| 20 | 0.54 | 555.81 | 0.79 | 602.41 | 0.82 | 636.20 | 2.26 | 799.90 |
| 30 | 0.29 | 370.33 | 0.37 | 401.31 | 0.39 | 423.83 | 0.83 | 532.37 |
| 40 | 0.23 | 277.71 | 0.27 | 300.92 | 0.28 | 317.80 | 0.48 | 399.00 |

TABLE 2

Attenuation and phase differences between two materials

| Energy, (keV) | Glandular - Adipose | | Skin - Glandular | | 0.2 Hydroxyapatite - Glandular | |
|---|---|---|---|---|---|---|
| | $\|\mu_G - \mu_A\|$, (1/cm) | $\|\phi_G - \phi_A\|$, (rad/cm) | $\|\mu_S - \mu_G\|$, (1/cm) | $\|\phi_S - \phi_G\|$, (rad/cm) | $\|\mu_{HA} - \mu_G\|$, (1/cm) | $\|\phi_{HA} - \phi_G\|$, (rad/cm) |
| 20 | 0.25 | 46.60 | 0.03 | 33.79 | 1.48 | 197.49 |
| 30 | 0.08 | 30.98 | 0.02 | 22.52 | 0.46 | 131.06 |
| 40 | 0.04 | 23.21 | 0.01 | 16.89 | 0.21 | 98.08 |

In a PCI system equipped with a polychromatic x-ray source, the transmittance of an exposure can be expressed as:

$$T = \frac{\int_E S(E)R(E)\exp\left(-\int \mu(E, r)dr\right)dE}{\int_E S(E)R(E)dE} \quad (4)$$

where E represents photon energy, S(E) is the energy dependent quanta distribution of the x-ray spectrum, R(E) is the spectral responsivity of the detector, and μ(E) is the spectral attenuation of the object, and r is the distance or path length along which an x-ray propagates. Typically, the equation (4) can be rewritten in terms of a system weighting factor W(E):

$$T = \int_E W(E)\exp\left(-\int \mu(E, r)dr\right)dE \quad (5)$$

where $$W(E) = \frac{S(E)R(E)}{\int_E S(E)R(E)dE}$$

The spectral response function, R(E), is primarily a detector property and it can be modeled, or measured experimentally. The spectral distribution of the quanta, S(E), which in a similar way can be either modeled or measured, is a property of the x-ray source. It depends on the x-ray tube's anode material, cathode voltage, and inherent and additional filtrations used in the imaging system (FIG. 3) during image acquisition.

For an x-ray beam passing through several materials of an object, the integral of linear attenuation in Equation (4) can be expressed as follows:

$$\int \mu(E, r)dr = \int \sum_m \mu_m(E, r)dr \quad (6)$$

where m represents some material. Similar to linear attenuation, the phase shift can also be represented as the summation over different materials. Using the example of a human breast, the following system of equations can be written:

$$\begin{cases} \mu(E) \cdot t = \mu_a(E) \cdot t_a + \mu_g(E) \cdot t_g \\ \varphi(E) \cdot t = \varphi_a(E) \cdot t_a + \varphi_g(E) \cdot t_g \end{cases} \quad (7)$$

where $t=t_a+t_g$ is the distance that an x-ray beam traveled in the object, $t_a$ and $t_g$ are the thicknesses of adipose and glandular tissues, respectively. Here $\mu_a$ and $\mu_g$ are the linear attenuations per unit of length (thickness), and $\phi_a$ and $\phi_g$ are the phase shifts per unit of length, where subscripts a and g represent adipose and glandular tissues, respectively.

The system of equations (7) can be programmably solved directly for thicknesses of adipose and glandular materials. However, the presence of nonlinear effects such as beam hardening and x-ray scatter may yield significant deviations in the results generated thereby. Nonlinear inverse functions (e.g., "thickness" functions) can be used to fit data using standard fitting techniques (e.g., nonlinear least-squares Levenberg-Marquardt minimization algorithm).

In one embodiment of the present invention, a single PCI scan using a PCI radiographic imaging system as described herein will generate image information of an object that is captured by a digital detector and that may be processed according to the equations described herein to generate two images: an absorption image and a phase shift image of the exposed object. Both images may be used to perform a two-material discrimination task or algorithm.

In one embodiment, an x-ray beam is fired from an x-ray source in the PCI radiographic system and passes through a first material of the object, material 1 of thickness $t_1$, and through a second material of the object, material 2 of thickness $t_2$. This embodiment can be modeled by rewriting equation (7) in the following form:

$$\begin{cases} f(t_1, t_2) = \mu_1(E) \cdot t_1 + \mu_2(E) \cdot t_2 \\ g(t_1, t_2) = \varphi_1(E) \cdot t_1 + \varphi_2(E) \cdot t_2 \end{cases} \quad (8)$$

where absorption (or linear attenuation) and phase shift measurements are denoted as $\mu(E) \cdot t \equiv f(t_1, t_2)$ and $\varphi(E) \cdot t \equiv g(t_1, t_2)$, respectively. Then the inverse thickness solution can be expressed as:

$$\begin{cases} P_{t_1}(f, g) - t_1 = 0 \\ P_{t_2}(f, g) - t_2 = 0 \end{cases} \quad (9)$$

where $P_{t_1}$ and $P_{t_2}$ are linear polynomial functions of f and g. For polyenergetic x-ray spectra the surfaces F(f,g) and G(f,g) can be used instead, such that the following is true:

$$\begin{cases} A_F - B_F F(f, g) - C_F F(f, g)^2 = 0 \\ A_G - B_G G(f, g) - C_G G(f_1, g)^2 = 0 \end{cases} \quad (10)$$

Here surfaces A, B, and C can be represented by second order polynomials (the F and G subscripts are dropped for clarity):

$$\begin{cases} A = a_0 + a_1 f + a_2 g + a_3 f^2 + a_4 fg + a_5 g^2 \\ B = b_0 + b_1 f + b_2 g \\ C = c_0 \end{cases} \quad (11)$$

or third order:

$$\begin{cases} A' = A + a_6 f^3 + a_7 f^2 g + a_8 fg^2 + a_9 g^3 \\ B' = B + b_3 f^2 + b_4 fg + b_5 g^2 \\ C' = C + c_1 f + c_2 g \end{cases} \quad (12)$$

The thickness functions F and G are found by programmably solving equation (7). For example, for F:

$$F = \frac{2A}{\sqrt{B^2 + 4AC} + B} \quad (13)$$

Two-material decomposition may be performed by incorporating absorption (attenuation) and phase shift data from a single PCI scan, according to equation (5). The technique requires a set of experimentally obtained calibration points for both attenuation and phase measurements. As a result of the calibration, appropriate a and b polynomial coefficients are used for the attenuation thickness function F and phase thickness function G.

As described herein, PCI may be performed using a number of different techniques. In one embodiment, the three-grating based DPCI system (FIG. 3) using Talbot-Lau interferometry principles is used, although other described techniques may be used. The source grating G0, having a period $p_0$ (or pitch) and slot size (width) s, may allow the use of a large incoherent x-ray source (e.g., standard broadband x-ray tube) by creating an array of individually coherent line sources that can provide sufficient spatial coherence for generating the interferometric contrast. A filter F and collimator C may also be used. The phase grating G1, having period $p_1$ smaller than $p_0$, may operate as a beam splitter and divide the incoming beam essentially into the ±1 diffraction orders. These two ±1 diffracted beams interfere and form a periodic interference pattern I, which repeats itself at specific distances, which may be referred to herein as Talbot distances. Furthermore, an analyzer grating G2, having period $p_2$ smaller than $p_1$, can be placed at one of such Talbot distances to modulate a moiré fringe pattern in the plane of the flat panel digital x-ray detector D placed directly behind the G2 grating. The x-ray source focal spot, $G_0$, an object under study, $G_1$, $G_2$ and the detector D are aligned so that x-rays emitted by the x-ray source pass through $G_0$, the object under study, $G_1$, $G_2$ and then the attenuated and phase shifted x-rays are captured at the detector D. Such a radiographic imaging system may be realized both for projection type of imaging and computed tomography (CT).

Figure 4:
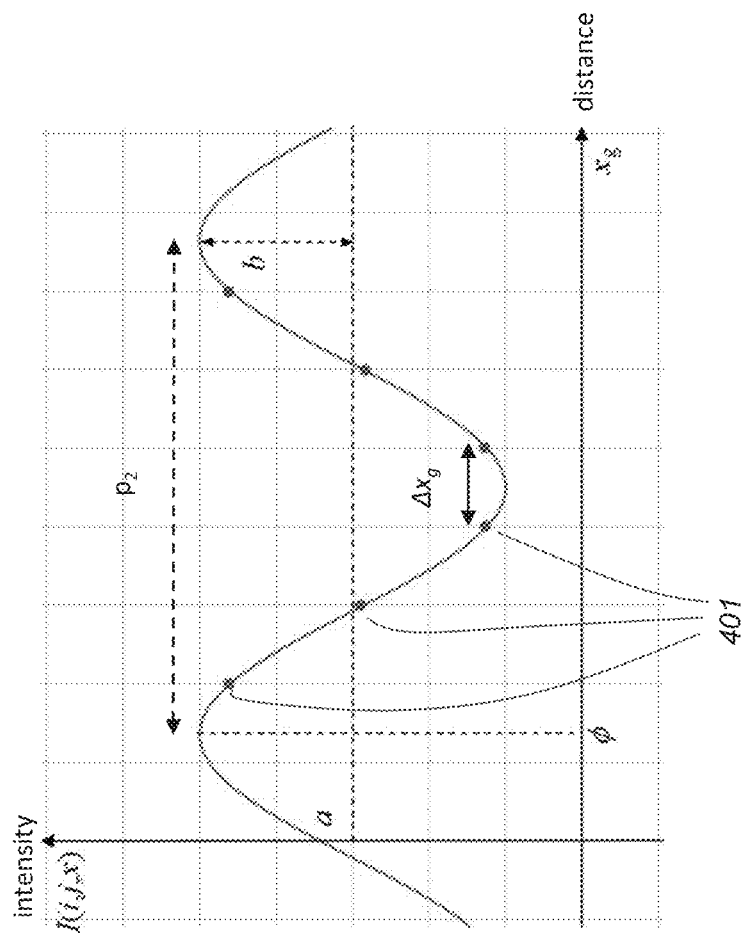
FIG. 4 is a graph plotting the intensity curve formed by stepping absorption grating G2 in direction x relative to phase grating G1 of the system of FIG. 3.

With respect to FIG. 4, the data acquisition technique in DPCI systems typically requires a plurality of x-ray exposures, as described herein. One of the acquisition techniques, which may be utilized with no loss of generality, is called phase stepping. It involves lateral stepwise movement or displacement in a form of discrete stepping of one of the gratings with respect to the other gratings and the x-ray detector (e.g., stepping of G2 grating parallel to x axis) by a fraction (Δx) of the respective grating pitch (or period, e.g., $p_2$) for each step. As a result of such multiple displacements, or steps, over a total pitch of the moved grating (e.g., $p_2$), each pixel of the x-ray detector D receives and measures a portion of the periodic sinusoidal intensity curve, as shown in FIG. 4. With respect to FIG. 4, $\Delta x_g$ represents a grating step size, a the mean intensity, b the amplitude of the intensity curve, $\phi$ the phase change, and six exemplary points 401 the intensity measured by a representative pixel at each of the six phase steps, although the number of phase steps per cycle may vary. The reconstruction methods described herein (for example, but not limited to, Fourier based) take advantage of such intensity oscillations (i.e., intensity curves) to extract the following basis images: a transmittance image, a differential phase image, and a darkfield (or visibility) image. Integration of a differential phase image along the differential direction yields an actual phase shift experienced by an x-ray passing through the object.

In one embodiment, as an example of material decomposition, we may solve a two-material differentiation in a projection-based PCI scan of a human breast. In this embodiment, the differentiation between two major components of the breast, adipose and glandular tissues, is targeted. A breast density, which may be selectively defined as a ratio of glandular tissue to total amount of breast tissue (i.e., glandular and adipose summed together), may be assessed or calculated. It is known to those skilled in the art that breast density is correlated with cancer development in the breast, and therefore the assessment of breast density is an important task for cancer prevention.

Figure 5B:
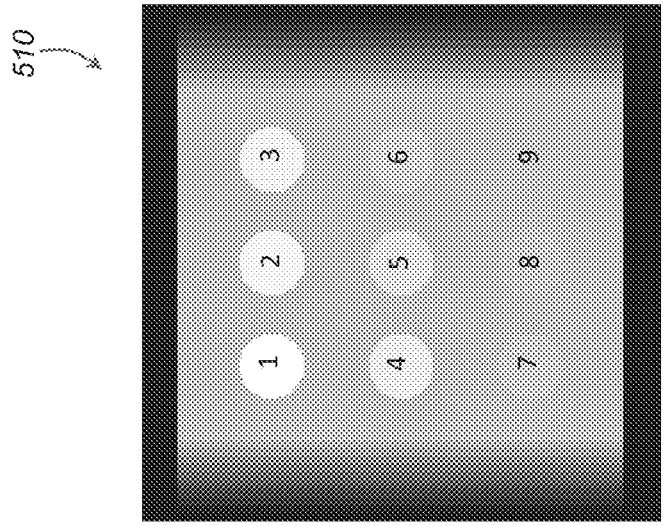
FIGS. 5A-5B are diagrams of a digital phantom used for two-material decomposition of breast tissue, wherein 5A is a 3D view of the digital phantom and 5B a projection onto an xy plane in units of linear attenuation, 1/cm.
Figure 5A:
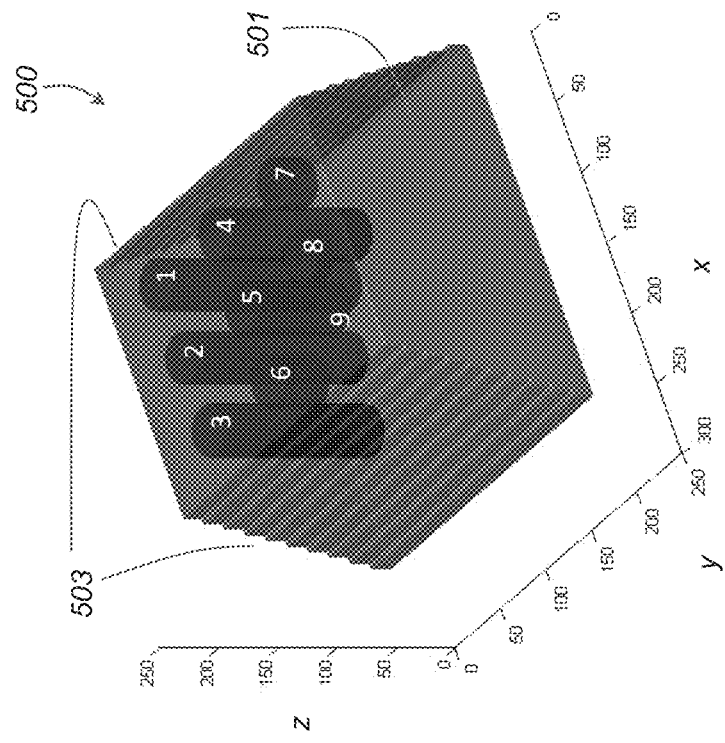

FIG. 5A illustrates an exemplary digital phantom used in simulations for breast density assessment. The phantom 500 consists of a slab 501 made of adipose material with stepped sides 503 and cylindrical pillar inserts (enumerated in FIG. 5A from 1 to 9) made of glandular material. The height of each pillar varies and was chosen such that the amount of glandular material in the pillars changes from about 100% to about 0% corresponding to the numbers from 1 to 9. The phantom was assigned linear attenuation and phase shift values, which were estimated according to equations (1)-(3). Then the x-ray beam was propagated parallel to the z axis to form an xy projection image 510 of the phantom 501, in units of linear attenuation, i.e., 1/cm, as shown in FIG. 5B. The direction of the PCI scan was chosen to be parallel to the x axis. The steps 503 in the phantom 500 were oriented to vary in the x-direction in order to avoid phase wrapping, which occurs when phase change between two neighboring pixels exceeds 2π.

To simulate the formation of DPCI images, the mathematical rationale described herein was employed. The digital detector's photosensitive pixels are assumed to be arranged in rows and columns that may be represented, or addressed, as an array of i,j coordinates.

i) In the case of the open field measurement (i.e., no object present on the pass of x-rays) the signal oscillation curve (or intensity curve) I for a detector pixel (i,j) is expressed as:

$$I_b(i, j, x_g) = a_b(i, j) + b_b(i, j)\cos\left(\frac{2\pi}{p_2}x_g + \phi_b(i, j) + \frac{2\pi}{p_2}n\Delta x_g\right) \quad (14)$$

where a is the average intensity, b is the signal amplitude, $x_g$ is the lateral position of the grating at step n of phase stepping distance $\Delta x_g$ (see FIG. 4 and associated description above).

ii) In the case of the object scan, equation (14) is changed to:

$$I_s(i, j, x_g) = \quad (15)$$
$$T_s(i, j) \cdot \left[a_b(i, j) + b_b(i, j)\cos\left(\frac{2\pi}{p_2}x_g + \phi_b(i, j) + \phi_s(i, j) + \frac{2\pi}{p_2}n\Delta x_g\right)\right]$$

Here, $T_s$ is the transmittance and $\phi_s$ is the change of the phase of an x-ray beam when it passes through the object.

To obtain attenuation and phase calibration points the thickness of adipose slab 501 (as shown in FIG. 5A) was altered between 10 to 80 mm with a step of 10 mm. In other words, eight phantom slabs with different total thickness were used. Each of the phantom slabs contained glandular pillar inserts with different glandular to adipose ratio, as described above with reference to glandular pillar inserts 1 through 9 of FIG. 5A.

Figure 6:
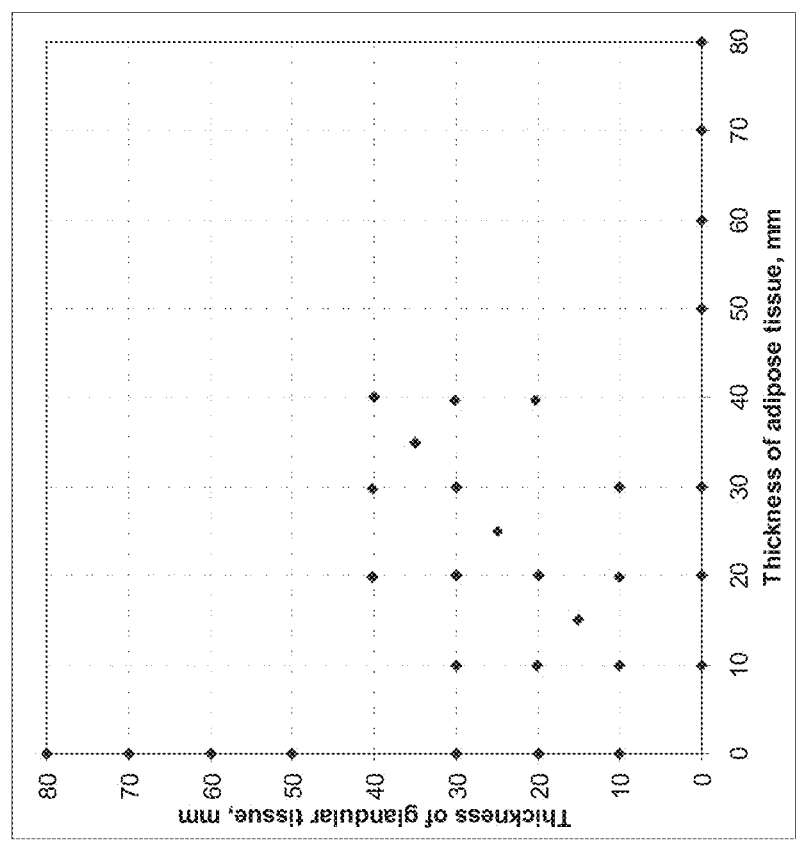
FIG. 6 is plot of thicknesses of glandular and adipose tissues used for calibration.

FIG. 6 shows the thicknesses (units of mm.) of adipose and glandular materials used in the calibration. For each of the calibration points of FIG. 6 a digital phantom 500 as shown in FIG. 5A was projected onto the xy plane and stepped n times (e.g., n=8) according to equations (14) and (15). Transmittance T and phase φ were measured and calculated using the system of equations (2). A cascaded system analysis (CSA) was used to access the noise level generated in the detector when an x-ray spectrum of 40 kVp is used. The CSA included simulation of: 1) x-ray quanta incident on the charge integrating detector; 2) interaction of x-ray quanta in a $Gd_2O_2S$ converter; 3) generation and emission of optical quanta in the converter; 4) spatial spreading of optical quanta in the converter; 5) coupling of optical quanta; and 6) integration of quanta by photodiode. A Fourier based reconstruction was then applied, in particular, for each pixel (if), an oscillation curve (or intensity curve) was expressed by a Fourier series:

$$I_s(i, j, x_g) \approx a_s(i, j) + b_s(i, j)\cos\left(\frac{2\pi}{p_2}x_g + \phi_s(i, j)\right) \quad (16)$$

$$I_b(i, j, x_g) \approx a_b(i, j) + b_b(i, j)\cos\left(\frac{2\pi}{p_2}x_g + \phi_b(i, j)\right) \quad (17)$$

Here, Equation (16) represents the intensity measurement with object present, while Equation (17) refers to measurement without an object (or reference scan). Applying inverse Fourier transformation the following images were obtained:

1) transmittance image:

$$T(i, j) = \frac{a_s(i, j)}{a_b(i, j)} \quad (18)$$

2) dark-field image:

$$V(i, j) = \frac{b_s(i, j)/a_s(i, j)}{b_b(i, j)/a_b(i, j)} \quad (19)$$

3) differential phase contrast image:

$$\left(\frac{\partial \varphi}{\partial x}\right)_{i,j} = \frac{p_2}{\lambda d_n}(\phi_s(i, j) - \phi_b(i, j)) \quad (20)$$

4) integrated phase contrast image:

$$\varphi_{i,j} = \frac{p_2}{\lambda d_n}\int (\phi_s(i, j) - \phi_b(i, j))dx \quad (21)$$

An example of the reconstructed projection images of attenuation and phase are shown in FIGS. 7A and 7B, respectively. The phase image FIG. 7B exhibits characteristic streak artifacts, which originate from integration of noisy differential phase image, i.e., according to equation (21). Such artifacts can be removed by different image smoothing techniques or regularized integration operation.

Furthermore, the thickness combinations of adipose and glandular tissues shown in FIG. 6 were fit by second order polynomial surfaces as described by equation (11) with f≡μ·t and g≡φ·t, where t is a total thickness and μ (1/cm) and φ (rad/cm) are defined per unit of length. The results of the fits are presented in Table 3. It should be noted that third order polynomial surfaces (Equation (12)) or other n-th order polynomial surfaces can be used instead.

TABLE 3

Fitting coefficients of second order polynomials for adipose and glandular materials.

| Material | $a_0$ | $a_1$ | $a_2$ | $a_3$ | $a_4$ | $a_5$ | $b_0$ | $b_1$ | $b_2$ |
|---|---|---|---|---|---|---|---|---|---|
| Adipose | 0.18442 | −149.099 | 0.14362 | 25.60206 | −0.0025 | −2.13 × $10^{-5}$ | 1 | −0.17329 | −1.48 × $10^{-4}$ |
| Glandular | −0.32609 | 137.8432 | −0.10926 | −29.3882 | 2.49 × $10^{-4}$ | 1.83 × $10^{-5}$ | 1 | −0.21088 | −1.70 × $10^{-4}$ |

Figure 8B:
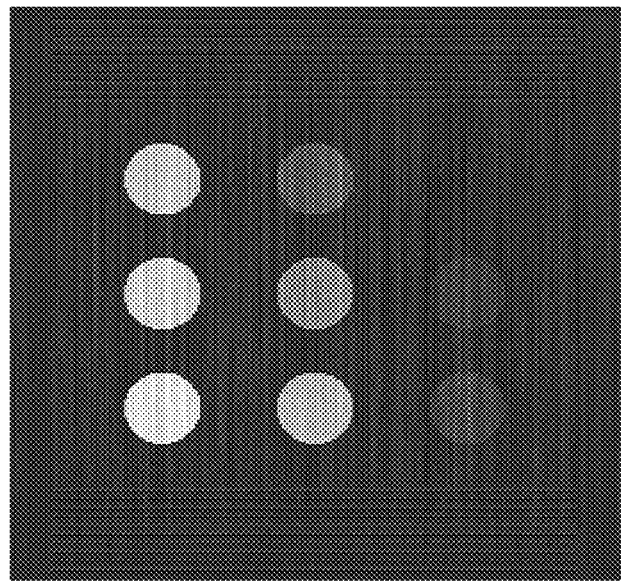
FIGS. 8A-8B are diagrams of an exemplary reconstructed adipose (left) and glandular (right) thicknesses for a 5 cm breast phantom shown in FIG. 5B.
Figure 8A:
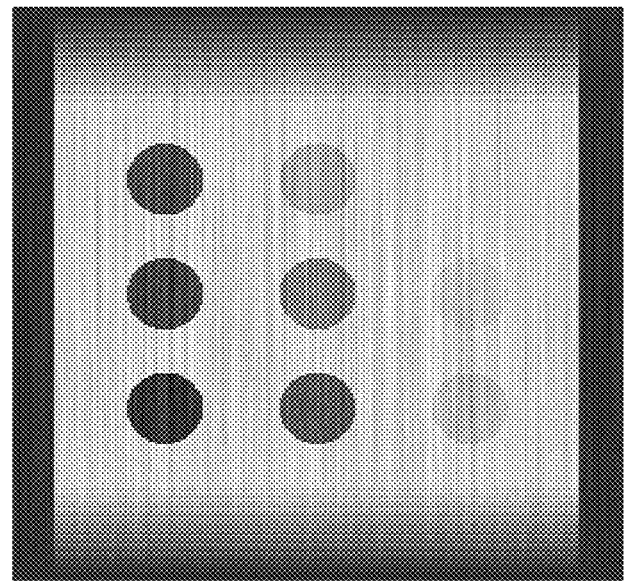

When the object with unknown distributions of materials of interest (such as adipose and glandular) is scanned, the f=μ·t and g=φ·t measurements are used in a polynomial utilized during calibration together with appropriate fit coefficients. An example of differentiation between adipose and glandular tissues from a single PCI scan of a 5 cm breast phantom is shown in FIGS. 8A-8B, respectively. The pillars numbered from 1 to 9, in the left-to-right order shown in FIG. 5B, were filled with glandular (G) and adipose (A) materials in G/A ratios of 0, 0.1, 0.15, 0.25 0.5, 0.75, 0.85, 0.9, and 1, respectively.

Figure 9:
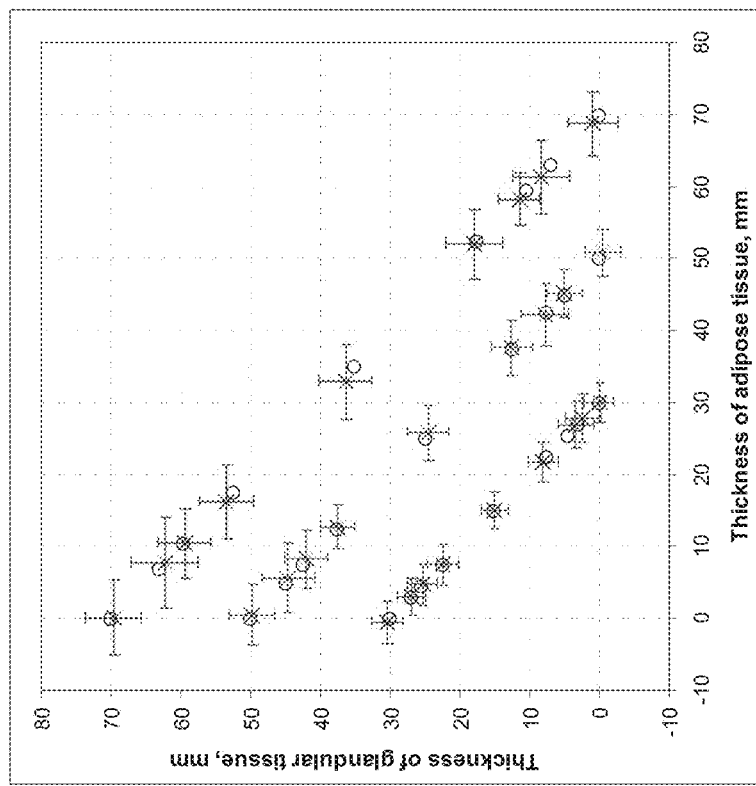
FIG. 9 is a plot of a thickness map, showing different points that represent a particular combination of glandular and adipose tissues, whereby the points that were defined, or provided by a digital phantom, are displayed as circles, while calculated points are displayed as asterisks (overlaid combination of + and x)

FIG. 9 shows exemplary calculated thicknesses of adipose and glandular tissues superimposed over adipose and glandular thicknesses defined in a digital phantom. Each point in the plot of FIG. 9 represents a particular combination percentage of glandular and adipose tissues. Three different thicknesses of digital phantom were used: 30, 50, and 70 cm. Defined (or given) values are represented by circles, while calculated values are shown as asterisks, or stars, with their corresponding error bars (superimposed × and +, with the + extended by an error margin).

Breast density can be calculated as a ratio of glandular thickness to total thickness, i.e., adipose+glandular:

$$BD = \frac{t_g}{t_a + t_g} \cdot 100\% \tag{22}$$

Figure 10:
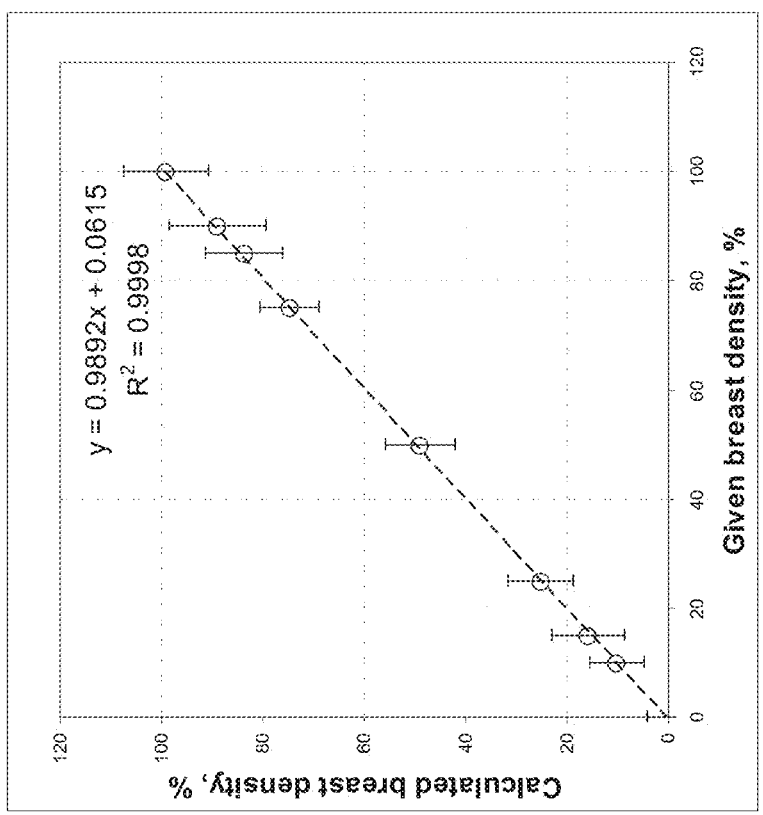
FIG. 10 is a plot showing a correlation between calculated breast density and known breast density for 5 cm thick breast tissue.

FIG. 10 shows the correlation of calculated breast density with breast density estimated from the known thicknesses of adipose and glandular tissues in a 5 cm breast phantom. Linear fit and regression analysis shows good correlation with $R^2$ value equal to about 99.98%. Relatively large error bars are observed due to severe streak artifacts present in the phase image (FIG. 7B). Note that streak artifacts can be reduced by different smoothing techniques or by regularization during integration of differential phase. Cleaner (i.e., with less noise) attenuation and phase images will yield smaller errors in adipose and glandular assessment and breast density calculations.

As will be appreciated by one skilled in the art, aspects of the present invention may be embodied as a computer system, programmed method, or computer program product. Accordingly, aspects of the present invention may take the form of an entirely hardware or apparatus embodiment, an entirely software or algorithmic embodiment (including firmware, resident software, micro-code, etc.), or an embodiment combining software and hardware aspects that may all generally be referred to herein as a "service," "circuit," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations and calculations, particularly of the disclosed equations, for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on a user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to apparatus (systems) and computer program products according to embodiments of the invention. It will be understood that steps of methods can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing and calculating the functions and algorithms specified in the description and/or equations.

These computer program instructions may also be stored in a computer readable medium that can direct a computer, other programmable data processing apparatus, or other devices to function in a particular manner, such that the instructions stored in the computer readable medium produce an article of manufacture including instructions which implement the functions and algorithms specified herein.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions, acts, and algorithms specified herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method comprising:
   radiographically scanning an object containing first type material and second type material using a phase contrast imaging (PCI) system;
   generating a plurality of radiographic images in response to the step of scanning, including generating a first image of the object that represents levels of absorption of radiographic radiation by the object and generating a second image that represents phase shifts of the radiographic radiation caused by the object; and
   calculating a proportional amount of the first type material in the object and calculating a proportional amount of the second type material in the object based on both a function of the absorption of radiographic radiation by the object per unit of length of the object and of the phase shifts of radiographic radiation caused by the object per unit of length of the object.

2. The method of claim 1, further comprising setting an x-ray source in the imaging system to emit radiographic energy having substantially one energy level.

3. The method of claim 1, wherein the step of scanning comprises firing an x-ray source emitting broadband radiographic energy aimed at the object.

4. The method of claim 3, wherein the step of scanning comprises moving a grating of the PCI imaging system through a plurality of discrete steps.

5. The method of claim 4, wherein the step of scanning further comprises stepping the grating of the PCI imaging system through a full cycle of an interference pattern generated by the PCI imaging system.

6. The method of claim 5, wherein the step of generating the first image of the object includes averaging intensity levels of the radiographic energy passing through the object at the plurality of discrete steps.

7. The method of claim 1, wherein the first type material consists of glandular tissue and the second type material consists of adipose tissue, and the method further comprises calculating a proportional amount of the glandular tissue in the object and a proportional amount of the adipose tissue in the object.

8. A phase contrast imaging system comprising:
   a radiographic energy source;
   a flat panel digital detector;
   an object to be imaged positioned between the radiographic energy source and the detector, the object containing first type material and second type material; and
   means for calculating a proportional amount of a first type of material in the object and a proportional amount of a second type of material in the object based on both a function of the absorption of radiographic energy by the object per unit of length of the object and of the phase shifts of radiographic energy caused by the object per unit of length of the object,
   wherein the source and detector are configured to radiographically expose the object containing the first type material and the second type material to produce a plurality of images of the exposed object, and
   wherein a first one of the produced images comprises image data representing the object's attenuation of the radiographic energy and a second one of the produced images comprises image data representing a phase shift of the radiographic energy passing through the object.

9. The system of claim 8, further comprising three gratings configured to produce the plurality of images of the exposed object, wherein the object is positioned between two of the gratings.

10. The system of claim 9, wherein the radiographic energy source is a broadband x-ray source.

11. The system of claim 9, wherein the radiographic energy source is configured to emit radiographic energy having substantially one energy level.

12. The system of claim 10, wherein the system is configured to move one of the gratings a plurality of discrete steps while radiographically exposing the object.

13. The system of claim 12, wherein said one of the gratings comprises a plurality of equally sized slots and wherein the system is configured to move said one of the gratings the plurality of discrete steps totaling a distance of one slot width.

14. The system of claim 13, wherein the image data representing the object's attenuation of the radiographic energy is based on an average attenuation by the object of radiographic energy at the discrete steps.

15. The system of claim 8, wherein the first type of material consists of glandular tissue and the second type of material consists of adipose tissue.

* * * * *